United States Patent
Blau et al.

(10) Patent No.: US 10,039,606 B2
(45) Date of Patent: Aug. 7, 2018

(54) ROTATIONAL POSITION DETERMINATION

(71) Applicant: Stryker European Holdings I, LLC, Kalamazoo, MI (US)

(72) Inventors: Arno Blau, Staufen im Breisgau (DE); Bernd Simon, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/431,848

(22) PCT Filed: Sep. 27, 2012

(86) PCT No.: PCT/EP2012/004102
§ 371 (c)(1),
(2) Date: Mar. 27, 2015

(87) PCT Pub. No.: WO2014/048447
PCT Pub. Date: Apr. 3, 2014

(65) Prior Publication Data
US 2015/0265361 A1    Sep. 24, 2015

(51) Int. Cl.
*A61B 19/00* (2006.01)
*A61B 17/17* (2006.01)
(Continued)

(52) U.S. Cl.
CPC .......... *A61B 19/50* (2013.01); *A61B 17/1703* (2013.01); *A61B 17/1725* (2013.01);
(Continued)

(58) Field of Classification Search
CPC ....... G06T 7/004–7/0048; A61B 19/50; A61B 17/1703; A61B 17/1725; A61B 17/1733;
(Continued)

(56) References Cited

U.S. PATENT DOCUMENTS

| | | |
|---|---|---|
| 4,475,545 A | 10/1984 | Ender |
| 4,622,959 A | 11/1986 | Marcus |
| | (Continued) | |

FOREIGN PATENT DOCUMENTS

| | | |
|---|---|---|
| CN | 1203435 A | 12/1998 |
| CN | 1424673 A | 6/2003 |
| | (Continued) | |

OTHER PUBLICATIONS

Amir Herman et al., The International Journal of Medical Robotics and Computer Assisted Surgery, 5; 45-50, Dec. 29, 2008.
(Continued)

*Primary Examiner* — Jan Christopher Merene
*Assistant Examiner* — Steven Cotroneo
(74) *Attorney, Agent, or Firm* — Lerner, David, Littenberg, Krumholz & Mentlik, LLP

(57) ABSTRACT

A method and a device is provided for determining a rotational position of a first feature of a first bone section relative to a second feature of a second bone section, the method comprises the steps of determining a longitudinal axis of a bone and determining a plane extending perpendicular to the longitudinal axis of the bone, determining a first projected vector representing a first direction defined by a feature of the first bone section, determining a second projected vector representing a second direction defined by a feature of the second bone section, and determining an angle between the first projected vector and the second projected vector.

23 Claims, 6 Drawing Sheets

(51) Int. Cl.
*A61B 17/74* (2006.01)
*G06T 7/73* (2017.01)
*A61B 17/72* (2006.01)
*A61B 17/90* (2006.01)
*A61B 34/10* (2016.01)
*A61B 90/00* (2016.01)

(52) U.S. Cl.
CPC ........ *A61B 17/7233* (2013.01); *A61B 17/744* (2013.01); *A61B 34/10* (2016.02); *G06T 7/73* (2017.01); *A61B 17/72* (2013.01); *A61B 2017/90* (2013.01); *A61B 2034/104* (2016.02); *A61B 2034/107* (2016.02); *A61B 2090/3764* (2016.02); *A61B 2090/3966* (2016.02); *F04C 2270/0421* (2013.01); *G06T 2207/10081* (2013.01); *G06T 2207/30008* (2013.01)

(58) Field of Classification Search
CPC ................. A61B 17/744; A61B 17/72; A61B 2034/101–2034/108
See application file for complete search history.

(56) References Cited

U.S. PATENT DOCUMENTS

| | | | |
|---|---|---|---|
| 5,122,141 A * | 6/1992 | Simpson | A61B 17/72 606/62 |
| 5,480,402 A | 1/1996 | Kim | |
| 5,533,143 A * | 7/1996 | Takeo | G06T 7/608 382/132 |
| 5,622,170 A * | 4/1997 | Schulz | A61B 5/0064 356/141.1 |
| 5,682,886 A | 11/1997 | Delp et al. | |
| 5,799,055 A | 8/1998 | Peshkin et al. | |
| 5,841,830 A | 11/1998 | Barni et al. | |
| 5,880,976 A | 3/1999 | DiGioia, III et al. | |
| 6,002,859 A | 12/1999 | DiGioia, III et al. | |
| 6,021,343 A | 2/2000 | Foley et al. | |
| 6,053,918 A | 4/2000 | Spievack | |
| 6,069,932 A | 5/2000 | Peshkin et al. | |
| 6,101,543 A | 8/2000 | Alden et al. | |
| 6,149,592 A | 11/2000 | Yanof et al. | |
| 6,198,794 B1 | 3/2001 | Peshkin et al. | |
| 6,205,411 B1 | 3/2001 | DiGioia, III et al. | |
| 6,221,074 B1 | 4/2001 | Cole et al. | |
| 6,226,548 B1 | 5/2001 | Foley et al. | |
| 6,285,902 B1 | 9/2001 | Kienzle, III et al. | |
| 6,341,231 B1 | 1/2002 | Ferre et al. | |
| 6,370,421 B1 | 4/2002 | Williams et al. | |
| 6,428,547 B1 | 8/2002 | Vilsmeier et al. | |
| 6,450,978 B1 | 9/2002 | Brosseau et al. | |
| 6,470,207 B1 | 10/2002 | Simon et al. | |
| 6,477,400 B1 | 11/2002 | Barrick | |
| 6,503,249 B1 | 1/2003 | Krause | |
| 6,510,241 B1 * | 1/2003 | Vaillant | A61B 6/583 345/419 |
| 6,535,756 B1 | 3/2003 | Simon et al. | |
| 6,674,883 B1 | 1/2004 | Wei et al. | |
| 6,697,664 B2 | 2/2004 | Kienzle, III et al. | |
| 6,701,174 B1 * | 3/2004 | Krause | A61B 17/025 378/21 |
| 6,711,432 B1 | 3/2004 | Krause et al. | |
| 6,718,194 B2 | 4/2004 | Kienzle, III | |
| 6,725,080 B2 | 4/2004 | Melkent et al. | |
| 6,747,646 B2 | 6/2004 | Gueziec et al. | |
| 6,810,280 B2 | 10/2004 | Strobel | |
| 6,856,826 B2 | 2/2005 | Seeley et al. | |
| 6,887,245 B2 | 5/2005 | Kienzle, III et al. | |
| 6,917,827 B2 | 7/2005 | Kienzle, III | |
| 6,922,581 B2 | 7/2005 | Kienzle, III | |
| 7,130,676 B2 | 10/2006 | Barrick | |
| 7,167,738 B2 | 1/2007 | Schweikard et al. | |
| 7,203,277 B2 | 4/2007 | Birkenbach et al. | |
| 7,235,076 B2 | 6/2007 | Pacheco | |
| 7,247,157 B2 | 7/2007 | Prager et al. | |
| RE40,176 E | 3/2008 | Peshkin et al. | |
| 7,392,076 B2 | 6/2008 | Moctezuma de La Barrera | |
| 7,427,200 B2 | 9/2008 | Noble et al. | |
| 7,427,272 B2 | 9/2008 | Richard et al. | |
| 7,567,834 B2 | 7/2009 | Clayton et al. | |
| 7,570,791 B2 | 8/2009 | Frank et al. | |
| 7,726,002 B2 | 6/2010 | Shimp et al. | |
| 7,887,545 B2 | 2/2011 | Fernandez et al. | |
| 7,914,532 B2 | 3/2011 | Shaver et al. | |
| 7,966,058 B2 | 6/2011 | Xue et al. | |
| 8,090,166 B2 | 1/2012 | Rappaport et al. | |
| 8,611,697 B2 | 12/2013 | Nathaniel et al. | |
| 9,111,180 B2 | 8/2015 | Rappaport et al. | |
| 2001/0036245 A1 | 11/2001 | Kienzle et al. | |
| 2002/0188194 A1 | 12/2002 | Cosman | |
| 2004/0009459 A1 | 1/2004 | Anderson et al. | |
| 2004/0030245 A1 | 2/2004 | Noble et al. | |
| 2004/0039259 A1 | 2/2004 | Krause et al. | |
| 2004/0082849 A1 | 4/2004 | Schweikard et al. | |
| 2004/0097922 A1 | 5/2004 | Mullaney | |
| 2004/0171924 A1 | 9/2004 | Mire et al. | |
| 2004/0230199 A1 | 11/2004 | Jansen et al. | |
| 2004/0243148 A1 | 12/2004 | Wasielewski | |
| 2004/0263535 A1 | 12/2004 | Birkenbach et al. | |
| 2005/0021043 A1 | 1/2005 | Jansen et al. | |
| 2005/0027304 A1 | 2/2005 | Leloup et al. | |
| 2005/0065617 A1 | 3/2005 | Moctezuma de la Barrera et al. | |
| 2005/0075632 A1 | 4/2005 | Russell et al. | |
| 2005/0288679 A1 | 12/2005 | Kienzle | |
| 2006/0015030 A1 | 1/2006 | Poulin et al. | |
| 2006/0064095 A1 | 3/2006 | Senn et al. | |
| 2006/0064106 A1 | 3/2006 | Fernandez | |
| 2006/0084867 A1 | 4/2006 | Tremblay et al. | |
| 2006/0095040 A1 | 5/2006 | Schlienger et al. | |
| 2006/0098851 A1 | 5/2006 | Shoham et al. | |
| 2006/0161059 A1 | 7/2006 | Wilson | |
| 2006/0173293 A1 | 8/2006 | Marquart et al. | |
| 2006/0241416 A1 | 10/2006 | Marquart et al. | |
| 2006/0281334 A1 | 12/2006 | Shin et al. | |
| 2007/0038059 A1 | 2/2007 | Sheffer et al. | |
| 2007/0038223 A1 | 2/2007 | Marquart et al. | |
| 2007/0161029 A1 * | 7/2007 | Li | C12Q 1/6834 435/6.12 |
| 2007/0161929 A1 * | 7/2007 | Maier | A61B 5/103 600/587 |
| 2007/0270680 A1 | 11/2007 | Sheffer et al. | |
| 2008/0018643 A1 | 1/2008 | Feilkas et al. | |
| 2008/0051910 A1 | 2/2008 | Kammerzell et al. | |
| 2008/0075348 A1 | 3/2008 | Rappaport et al. | |
| 2008/0089566 A1 | 4/2008 | Node-Langlois et al. | |
| 2008/0119725 A1 | 5/2008 | Lloyd | |
| 2008/0243191 A1 | 10/2008 | Tipirneni et al. | |
| 2008/0269596 A1 | 10/2008 | Revie et al. | |
| 2008/0281334 A1 | 11/2008 | Zheng et al. | |
| 2008/0294265 A1 | 11/2008 | Warkentine et al. | |
| 2008/0319448 A1 | 12/2008 | Lavallee et al. | |
| 2009/0209851 A1 * | 8/2009 | Blau | A61B 17/1703 600/426 |
| 2009/0234217 A1 | 9/2009 | Mire et al. | |
| 2010/0030219 A1 | 2/2010 | Lerner et al. | |
| 2010/0104150 A1 * | 4/2010 | Saint Felix | A61B 5/4504 382/128 |
| 2010/0168562 A1 | 7/2010 | Zhao et al. | |
| 2011/0019884 A1 | 1/2011 | Blau | |
| 2011/0184477 A1 | 7/2011 | Dell'Oca et al. | |
| 2011/0213379 A1 | 9/2011 | Blau et al. | |
| 2011/0313418 A1 * | 12/2011 | Nikonovas | A61B 17/62 606/56 |
| 2013/0060146 A1 * | 3/2013 | Yang | A61B 34/20 600/476 |

FOREIGN PATENT DOCUMENTS

| | | |
|---|---|---|
| CN | 101069640 A | 11/2007 |
| DE | 102005062610 A1 | 6/2007 |
| DE | 102005062611 A1 | 6/2007 |
| DE | 102007008521 A1 | 8/2007 |

(56) References Cited

FOREIGN PATENT DOCUMENTS

| | | |
|---|---|---|
| DE | 102007008522 A1 | 8/2007 |
| EP | 0738502 A2 | 10/1996 |
| EP | 1440664 A2 | 7/2004 |
| EP | 1491151 A1 | 12/2004 |
| EP | 1523950 A1 | 4/2005 |
| EP | 1859755 A2 | 11/2007 |
| EP | 1994914 A1 | 11/2008 |
| FR | 2895267 A1 | 6/2007 |
| GB | 2421187 A | 6/2006 |
| JP | 2000510730 A | 8/2000 |
| JP | 2005246059 A | 9/2005 |
| JP | 2008514296 A | 5/2008 |
| JP | 2010538753 A | 12/2010 |
| WO | 0209611 A2 | 2/2002 |
| WO | 2003105659 A2 | 12/2003 |
| WO | 2004069040 A2 | 8/2004 |
| WO | 2005087125 A2 | 9/2005 |
| WO | 2007073733 A1 | 7/2007 |
| WO | 2007095917 A2 | 8/2007 |
| WO | 2007095918 A1 | 8/2007 |
| WO | 2007095919 A2 | 8/2007 |
| WO | 2007124099 A2 | 11/2007 |
| WO | 2009087214 A1 | 7/2009 |
| WO | 2011002903 A2 | 1/2011 |
| WO | 2012007054 A1 | 1/2012 |
| WO | 2012084056 A1 | 6/2012 |

OTHER PUBLICATIONS

Communication from EP Application No. 10153136 dated Aug. 17, 2011.

Hofstetter et al., "Computer-Assisted Fluoroscopy-Based Reduction of Femoral Fractures and Antetorsion Correction", Computer Aided Surgery 5:311-325 (2000).

International Search Report for PCT/EP2009/050210 dated Jun. 16, 2009.

International Search Report for PCT/EP2010/060314 dated Apr. 6, 2011.

International Search Report for PCT/EP2012/004102 dated Feb. 27, 2013.

Jagannathan et al., Neurosurg Focus 20, 2, E9, pp. 1-6, 2006.

Joskowicz et al., IEEE Transactions on Medical Imaging, IEEE Service Center, Piscataway NJ, US, vol. 24, No. 5, May 1, 2005, pp. 624-635.

Schulz et al., "Evidence Based Development of a Novel Lateral Fibula Plate (VariAx Fibula) Using a Real CT Bone Data Based Optimization Process During Device Development", The Open Orthopaedics Journal, 6:1-7 (2012).

Thomas C. Kienzle III et al., "An Integrated CAD-Robotics System for Total Knee Replacement Surgery", IEEE, 1993.

Ziv Yaniv, Member, IEEE, and Leo Joskowicz, Senior Member, IEEE, Precise Robot-Assisted Guide Positioning for Distal Locking of Intramedullary Nails, IEEE Transactions on Medical Imaging, vol. 24, No. 5, May 2005.

U.S. Office Action for U.S. Appl. No. 13/810,299 dated Jun. 4, 2015.

Guoyan Zheng et al., Precise estimation of postoperative cup alignment from single standard X-ray radiograph with gonadal shielding, Proceedings of the 10th international conference on Medical image computing and computer-assisted intervention, Oct. 29-Nov. 2, 2007, Brisbane, Australia.

* cited by examiner

ROTATIONAL POSITION DETERMINATION

CROSS-REFERENCE TO RELATED APPLICATIONS

The present application is a national phase entry under 35 U.S.C. §371 of International Application No. PCT/EP2012/004102 filed Sep. 27, 2012, published as WO 2014/048447 A1 on Apr. 3, 2014, which is hereby incorporated herein by reference.

FIELD OF THE INVENTION

The invention relates to the field of computer assisted surgery. In particular, the invention relates to a method and a device for determining a rotational position of a first feature of a first bone section relative to a second feature of a second bone section of one bone. The method may be implemented as a computer program executable on a processing unit of the device.

BACKGROUND OF THE INVENTION

In a case in which a shaft of a long bone is fractured, a bone nail may be used to stabilize the parts of the bone during the healing of the fracture, wherein the bone nail may be inserted into a medullary channel of the bone in a longitudinal direction thereof. However, such a bone nail may allow a rotation of one part of the bone relative to another part of the bone, about the axis of the bone nail, at least until a locking screw is inserted through the bone nail in a lateral direction to fix the position of the rotatable part.

Accordingly, a physician should position the fractured parts as anatomically correct as possible. One approach may be to take into account features of the healthy counterpart of the fractures bone to provide information regarding how the parts of the fractured bone should be arranged. But this is difficult, since the bone of the counterpart is usually not visible.

SUMMARY OF THE INVENTION

It may be seen as an object of the invention to provide a method and a device for assisting a determination of an anatomical orientation of a first feature of a first bone section relative to a second feature of a second bone section. This is achieved by the subject-matter of each of the independent claims. Further embodiments are described in the respective dependent claims.

In general, a method is provided, namely a method for determining a rotational position of a first feature of a first bone section relative to a second feature of a second bone section, the method comprises the steps of determining a longitudinal axis of a bone and determining a plane extending perpendicular to the longitudinal axis of the bone, determining a first projected vector in the plane, for example by determining a first vector representing a first direction defined by a feature of the first bone section and projecting the first vector onto the plane, determining a second projected vector in the plane, the vector representing a second direction defined by a feature of the second bone section, and determining an angle between the first projected vector and the second projected vector.

Any bone, for example a bone at a hand or foot, in particular a long bone of the lower extremities, like the femur and the tibia, and of the upper extremities, like the humerus, may be subject to an embodiment of the method. That is, an orientation of a feature at for example the proximal section of a respective bone may be determined relative to a feature at the distal section of the respective bone. It is noted that such a determination of a feature may be performed based on gray scale image data which may be received for example from an x-ray imaging unit.

As used herein, the term "feature of a bone" refers to anything at a bone which may be suitable for determining a geometrical aspect, i.e. a point, a line, an arc, a center point, an axis, a cylinder surface, a ball surface, or the like, wherein such geometrical aspects are in particular suitable for a determination of a longitudinal axis and/or a vector. For example, a geometrical aspect of a femur may be the outer surface of the femur head, an axis defined by the neck between shaft and femur head, a longitudinal axis of the femur shaft, a most distal point on the bone surface, a line defined by the center points of the condyles, or a line defined by the most posterior points at the condyles. It will be understood that the other long bones provide other and/or comparable suitable geometrical aspects.

As used herein, the term "feature of a bone" may encompass any feature of an implant being already inserted into a bone or at least fixedly connected to a bone, said feature being suitable for determining a geometrical aspect as mentioned above.

As used herein, the term "projected vector" refers to a vector being projected on a plane, i.e. which results from a projection of a vector having any 3D orientation perpendicularly onto a plane. It is noted that a "projected vector" may also be achieved by a projection of only two points, for example end points, of a vector having any 3D orientation onto a plane, with the projected points defining the projected vector in the plane.

According to an embodiment, at least one of the longitudinal axis of the bone, the feature of the first bone section and the feature of the second bone section is determined on the basis of a 3D image of at least a section of the bone.

It will be understood that a 3D image, i.e. a volume image may be generated from a stack of 2D images oriented in one direction or based on a plurality of 2D projection images generated from different imaging angles.

According to another embodiment, at least one of the longitudinal axis of the bone, the feature of the first bone section and the feature of the second bone section is determined on the basis of a 2D image of at least a section of the bone, wherein the 2D image further includes a visualization of a reference body. The reference body may comprise a structure forming a characteristic 2D projection image for determining a 3D orientation of the reference body. In other words, based on one 2D projection image, a 3D orientation of the reference body can be determined, leading to a determination of a 3D orientation of a feature of a bone.

According to a further embodiment, the reference body is adapted to be fixedly connected to the bone.

As used herein, each of the terms "fixedly connected", "fixedly coupled" and "fixedly attached" encompasses a direct or an indirect connection of an element to another element. For example, a reference body may be directly attached at an implant or may be indirectly coupled to an implant, with for example an aiming device between the reference body and the implant. On the other hand, a reference body which is integrated into an implant, i.e. which can be considered as fixedly connected to the implant, may be considered as being indirectly coupled to a bone, i.e. via the implant.

According to an embodiment, the reference body may be at least a part of an implant. In other words, an implant which is adapted to be fixed at or in a bone may comprise elements which can be identified in an image of the bone or at least a section of the bone so that a vector may be determined based on the identified elements. For example, the elements may define points so that two elements may define a line or an axis, or the elements may define a contour so that a center axis may be determined.

According to an embodiment, the reference body defines an axis, i.e. the implant comprises an axis and the axis of the implant represents one of the longitudinal axis of the bone, the feature of the first bone section and the feature of the second bone section. In other words, based on the reference body, an axis or a vector may be determined. In case an implant is already implanted into or at a bone, a feature of the implant may be determined instead of a feature of the bone so that the feature of the implant may represent a feature of the bone.

According to yet another embodiment, the reference body is adapted to be fixedly connected to the first bone section while being visible in an image showing the second bone section.

As a first example, the reference body may be integrated into a leading end of a bone nail so that when a trailing end of the bone nail is already fixed to a first section of the bone, the reference body may be located within the second section of the bone and may thus be visible in an image of that second section.

As a second example, the reference body may be integrated into an aiming device for supporting an insertion of a locking screw through a bore in a leading end of a bone nail. Therefore, the aiming device may be adapted to be coupled to a trailing end of the bone nail and may extend outside the body of a patient as far as the bone nail extends inside the bone so that at least a portion of the aiming device can be visible in an image of the second section of the bone including the leading end of the bone nail.

According to an embodiment, the method does not comprise any step of connecting a reference body at a bone, in so far as it constitutes a treatment of a human or animal body by surgery.

According to another embodiment, a device for determining a rotational position of a first feature of a first bone section relative to a second feature of a second bone section, comprises a processing unit which is adapted to perform the steps of the method. Therefore, the processing unit may be adapted for determining a longitudinal axis of a bone based on received image data, and determining a plane extending perpendicular to the longitudinal axis of the bone, determining a first projected vector representing a first direction defined by a feature of the first bone section, based on received image data, determining a second projected vector representing a second direction defined by a feature of the second bone section, based on received image data, and determining an angle between the first projected vector and the second projected vector.

It is noted, that the processing unit may be realized by only one processor performing all the steps of the method, or by a group or plurality of processors, for example a system processor for processing the image data, a separate processor specialized on a determination of geometrical aspects, and a further processor for controlling a monitor for visualizing the result.

According to an embodiment, the device further comprises an imaging unit for providing 2D projection image data of at least a section of the bone. The imaging unit may be capable of generating images from different directions. Accordingly, the imaging unit of the device may be adapted to also provide 3D image data of at least a section of the bone.

According to yet another embodiment, the processing unit of the device is further adapted for identifying a reference body in a projection image and for determining a 3D orientation of the reference body.

According to a further embodiment, the device further comprises a reference body including an arrangement of elements which allows a reconstruction of a 3D orientation of the reference body based on a 2D projection image.

The device may further comprise input means for manually identifying geometrical aspects of a bone in an image. Such input device may be for example a computer keyboard, a computer mouse or a touch screen.

According to a further embodiment, a computer software is provided including sets of instructions which when executed on an appropriate device, causes the device to perform the steps of the method as described above.

A corresponding computer program is preferably loaded into a work memory of a data processor. The data processor or processing unit is thus equipped to carry out the method. Further, the invention relates to a computer-readable medium such as a CD-ROM at which the computer program may be stored. However, the computer program may also be presented over a network like the World Wide Web and can be downloaded into the working memory of the data processor from such a network.

It has to be noted that embodiments are described with reference to different subject-matters. In particular, some embodiments are described with reference to method type claims (computer program) whereas other embodiments are described with reference to apparatus type claims (system). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

Figure 1:
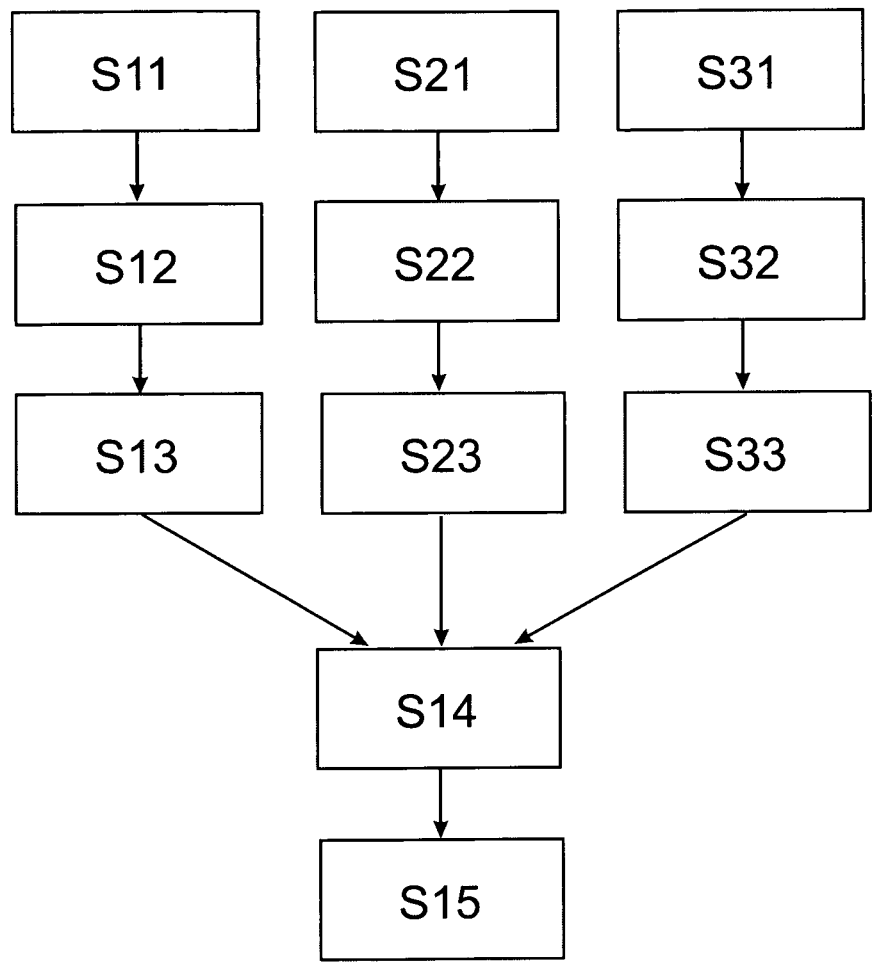
FIG. 1 shows a flow chart of steps of an embodiment of a method.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE EMBODIMENTS

The flow-chart in FIG. 1 illustrates the principle of the steps performed in accordance with one embodiment of the disclosed method. It will be understood that the steps described, are major steps, wherein these major steps might be differentiated or divided into several sub-steps. Furthermore, there might be also sub-steps between these major steps.

In accordance with one method, in step S11, an image of the bone is received. In step S12, the longitudinal axis of the bone is determined. In step S13, a plane is determined extending perpendicular to the longitudinal axis.

In step S21, an image of the bone is received. In step S22, a first feature is identified representing a direction, so that at least two points can be determined defining a first vector in step S23.

Comparable with steps S21 to S23, at least two points defining a second vector are determined in steps S31 to S33.

As used herein, the term "receiving an image" basically refers to the fact that at least one image is necessary to perform the subsequent steps. That is, the term "receiving an image" may encompass also a loading of an image from a data memory into a processing unit. There is no need to generate a new image to receive an image. Accordingly, each of the images received in steps S11, S21 or S31, may be any image suitable to identify a longitudinal axis of the bone, or a feature of the bone, i.e. a 3D image or a 2D image of at least the respective section of the bone, wherein the 2D image should additionally show a reference body.

On the other hand, it will be understood that only one image may be sufficient to determine the longitudinal axis as well as the first and second features of a bone, so that the same image may be received in steps S11, S21 and S31.

In step S14, at least two points of the first vector determined in step S23 and at least two points of the second vector determined in step S33 are projected onto the plane determined in step S13, thus defining a first projected vector and a second projected vector.

It is note that the points are preferably projected onto the plane in a direction perpendicular to the plane.

Finally, an angle between the first projected vector and the second projected vector is determined in step S15.

It should be noted that these method steps may be performed to determine an angle between features at opposed ends of one healthy bone, but may also be performed to check whether an angle between features at opposed ends of one fractured bone are anatomically correctly arranged relative to each other. For example, the method may firstly be performed on a healthy counterpart of a fractured bone to determine an anatomically correct angle related to one patient, and may secondly be performed on the fractured bone to support the attempt to correctly arrange parts of the fractured bone.

Figure 2:
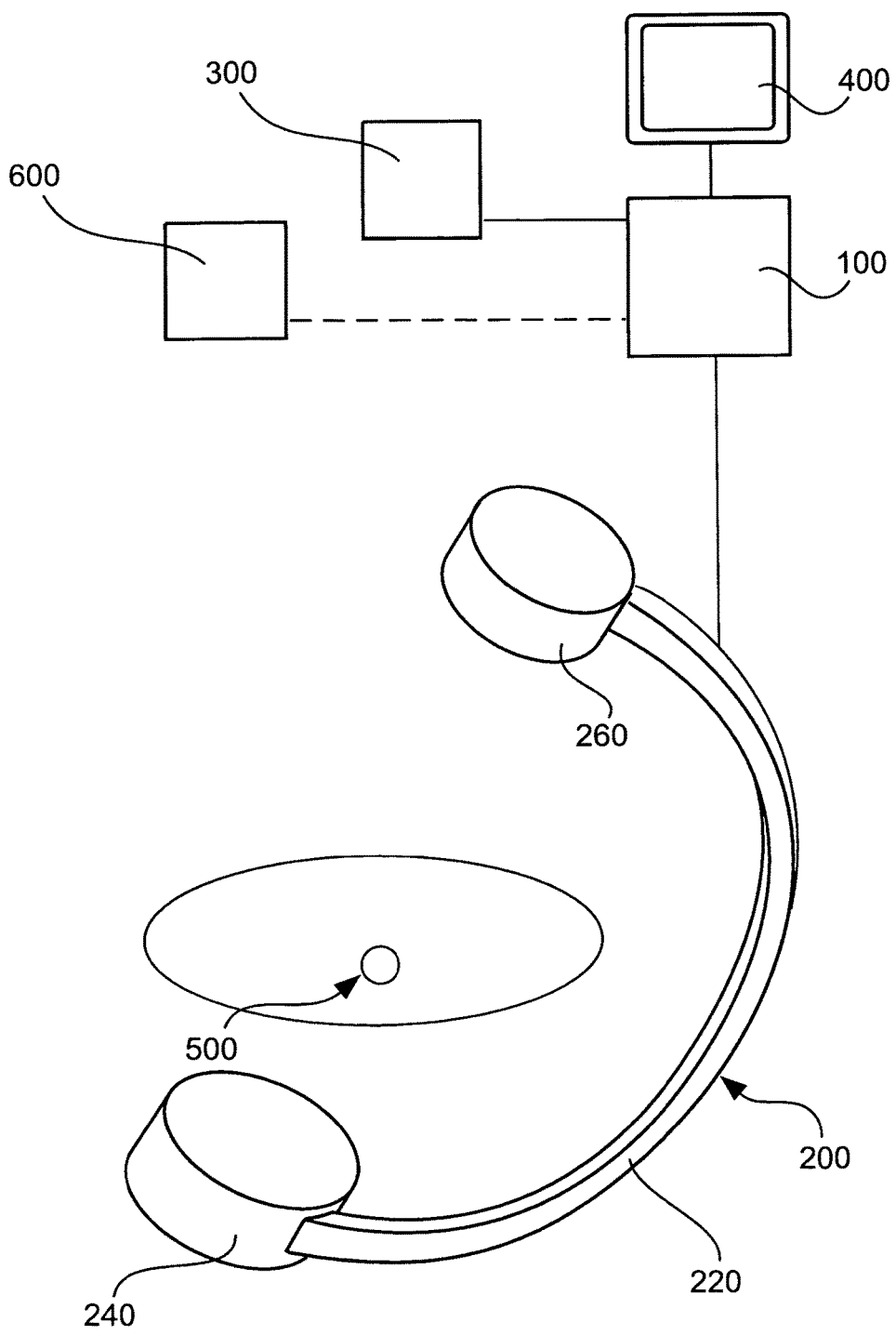
FIG. 2 shows a schematical illustration of a system.

FIG. 2 shows an exemplary embodiment of a device. Substantially, necessary for performing the steps of the method, a processing unit 100 together with a monitor 400 is part of the device.

An exemplary imaging device 200 includes an X-ray source 240, and an X-ray detector 260, wherein these two devices are mounted on a C-arm 220. It will be understood that the device may also comprise a non-invasive imaging modality like a computer tomography device, a magnetic resonance device, or an ultrasound device as imaging device instead of or additional to the shown C-arm based X-ray device.

Furthermore, the system in FIG. 2 includes an input device 300, by means of which for example a manual determination of a bone feature may be performed. Also shown is a connection (as dotted line) to a database 600, located for example in a network.

Finally, there is shown a region of interest 500. Within said region, for example a bone of a patient may be located which is subject to the method. Examples of (schematically) images from an imaging device 200, can be seen in FIGS. 3 and 6.

FIGS. 3 to 6 show schematically illustrations of exemplary images which may form a basis for performing the method. In this example, a rotational positioning of a first section 12, i.e. a proximal section relative to a second section 14, i.e. a distal section of a bone, i.e. a femur 10 is determined, with a fracture F in the shaft of the femur 10.

Figure 3:
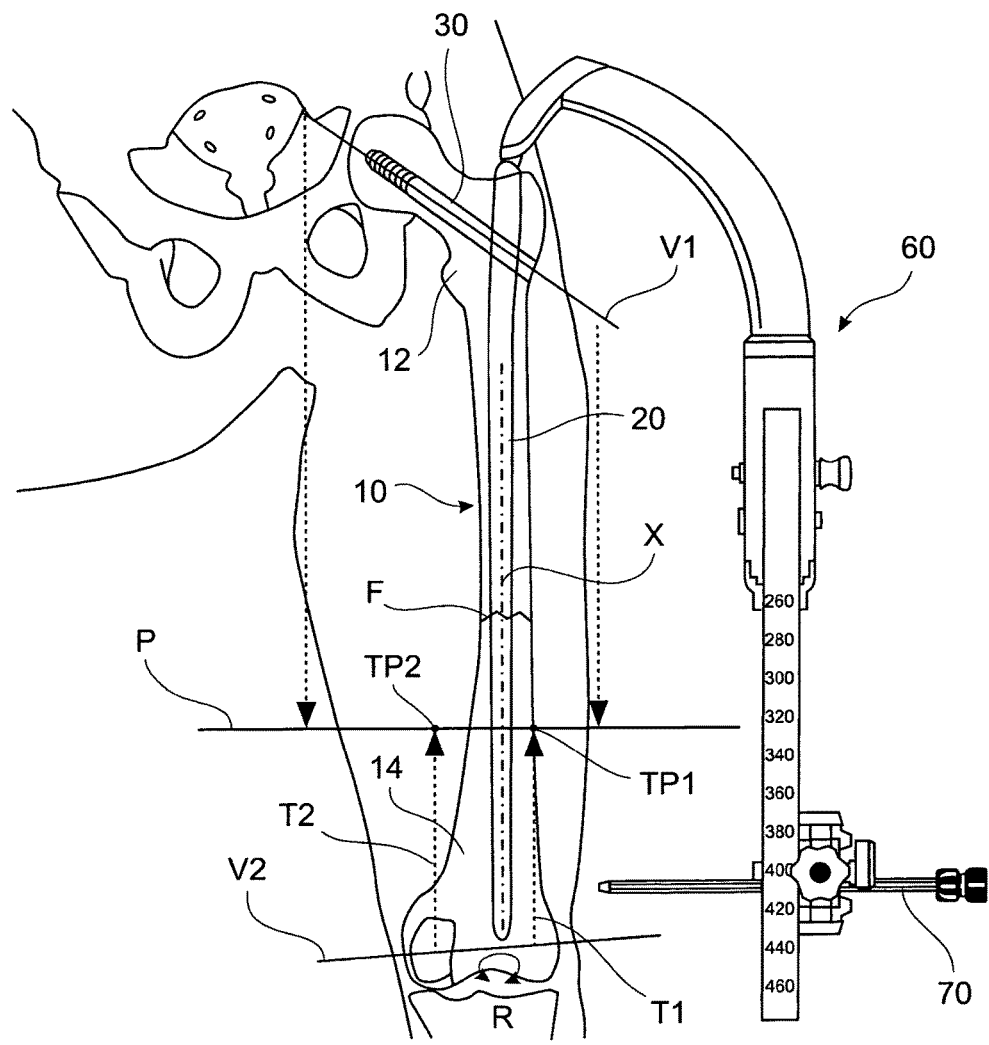
FIG. 3 shows an exemplary illustration of a femur in an anterior to posterior direction.

FIG. 3 is an image generated in an anterior to posterior direction, i.e. from above (assuming that the patient is lying on his/her back). FIG. 3 shows a situation in which a bone nail 20 is already inserted into a medullary channel of the femur 10 in a longitudinal direction of the femur. Furthermore, the proximal section 12 of the femur 10 is rotationally fixed relative to the bone nail 20 by means of a locking screw 30 inserted through a bore in the bone nail and into the head of the femur. Fixedly attached to the bone nail 20 is an aiming device 60 with a sleeve 70 for an insertion of a further locking screw to be inserted in the distal section 14 of the femur.

Due to the fracture F, the distal section 14 of the femur can be rotated relative to the proximal section 12 of the femur 10. This is indicated by the arrow R. The problem to be solved in this situation is to find the anatomically correct rotational position of the distal section 14, to avoid a malposition of the knee joint and the lower leg relative to the hip joint.

With the aim to determine the current position of the distal section 14 relative to the proximal section 12, a plane P perpendicular to the longitudinal axis of the bone (perpendicular to the drawing sheet), a first vector V1 and a second vector V2 may be firstly determined, wherein each of the two vectors represent a direction of a feature at the respective section of the femur.

It is noted that the vectors V1 and V2 are not shown as arrows, since it is irrelevant in which direction the vectors point, along the shown lines, respectively.

As a first approximation it can be assumed that the longitudinal axis X of the bone nail 20 is identical with the longitudinal axis of the shaft of the femur 10. A plane P extending perpendicular to the longitudinal axis of the bone nail 20 will be identical to a plane extending perpendicular to the shaft of the femur, as long as the longitudinal axes are congruent or at least parallel to each other. In case there exists a deviation of the longitudinal axis of the bone nail from the longitudinal axis of the femur shaft, the angle between the longitudinal axes would be so small that a resulting error in the determination of an angle between two projected vectors on the plane can be neglected. Therefore, the longitudinal axis X of the bone nail 20 which is easier to determine, may be utilized to determine the plane P.

Having a locking screw 30 already inserted into the neck and head of the femur 10, provides the possibility to utilize the axis of the locking screw as the first feature at the first section 12 of the femur 10. Accordingly, a first vector V1 may be determined based on the axis of the locking screw 30.

Based on the projection image as shown in FIG. 3, the longitudinal axis X and thus the plane P as well as the first vector V1 may be determined, wherein the known relation between for example the aiming device 60, when fixedly connected to the bone nail, and the axis of the through bore in the bone nail through which the locking screw has been inserted, may be taken into account to determine the 3D orientation of the first vector V1.

Additionally, the second vector V2 is shown in FIG. 3, although it would be difficult to determine the position and orientation of the second vector from an anterior-posterior image.

Indicated by dotted arrows, the method step of projecting at least two points of the first and second vectors onto plane P is visualized in FIG. 3.

Figure 4:
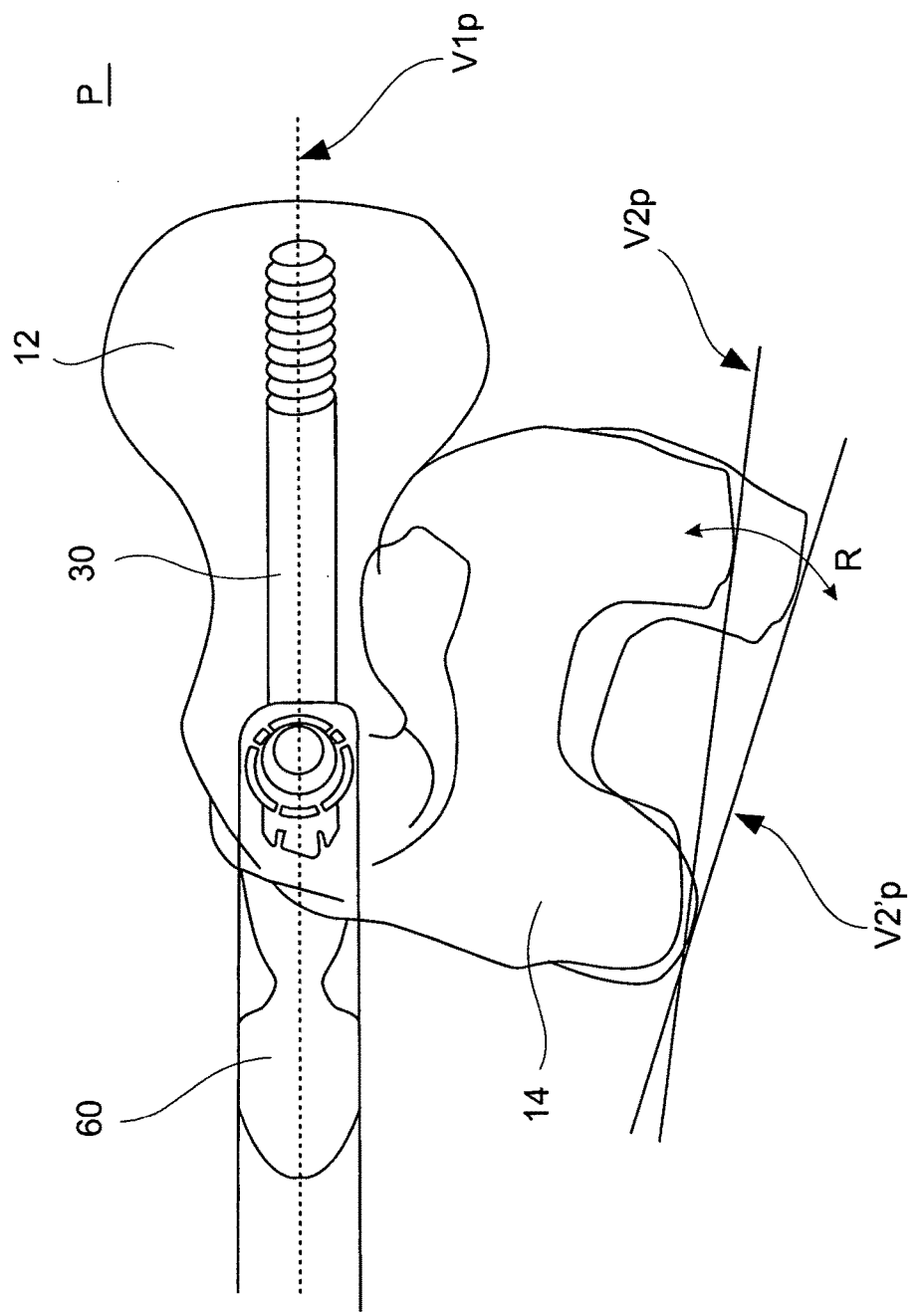
FIG. 4 shows an exemplary illustration of a femur in a proximal to distal direction.

In FIG. 4, a plan view onto plane P (identical with the drawing sheet) is shown together with features of the femur, i.e. the head of the femur at the first section 12 as well as the condyles at the second section 14 of the femur, as would be seen when viewed in a proximal to distal direction of the femur. FIG. 4 further shows a locking screw 30 extending from the bone nail into the head of the femur and an aiming device 60 which is fixedly connected to the bone nail and extends outside of the bone, i.e. the leg. It is noted that FIG. 4 is a constructed image for explanation purposes. Therefore, the soft tissue surrounding the femur is omitted in FIG. 4.

As can be seen in FIG. 4, the most posterior points at the condyles are used to determine a tangent line. The tangent line at the condyles serves to determine a second vector V2p at the second section 14 of the femur. At the first section 12 of the femur, the axis of the locking screw 30 is a basis for determining the first vector V1p.

Further visualized in FIG. 4 is the aspect that the second section 14 of the femur may be rotated relative to the first section 12 of the femur, about the longitudinal axis of the bone nail. Such a rotation is indicated by arrow R, causing for example a change of the orientation of the second vector V2p to an orientation of a vector V2'p.

Assuming that the orientation of the second vector V2p represents an anatomically correct position of the condyles, and that vector V2'p is an orientation as currently determined, it would be possible to determine the angle of rotation about which the second section 14 of the femur has to be rotated to achieve an anatomically correct arrangement.

Figure 5:
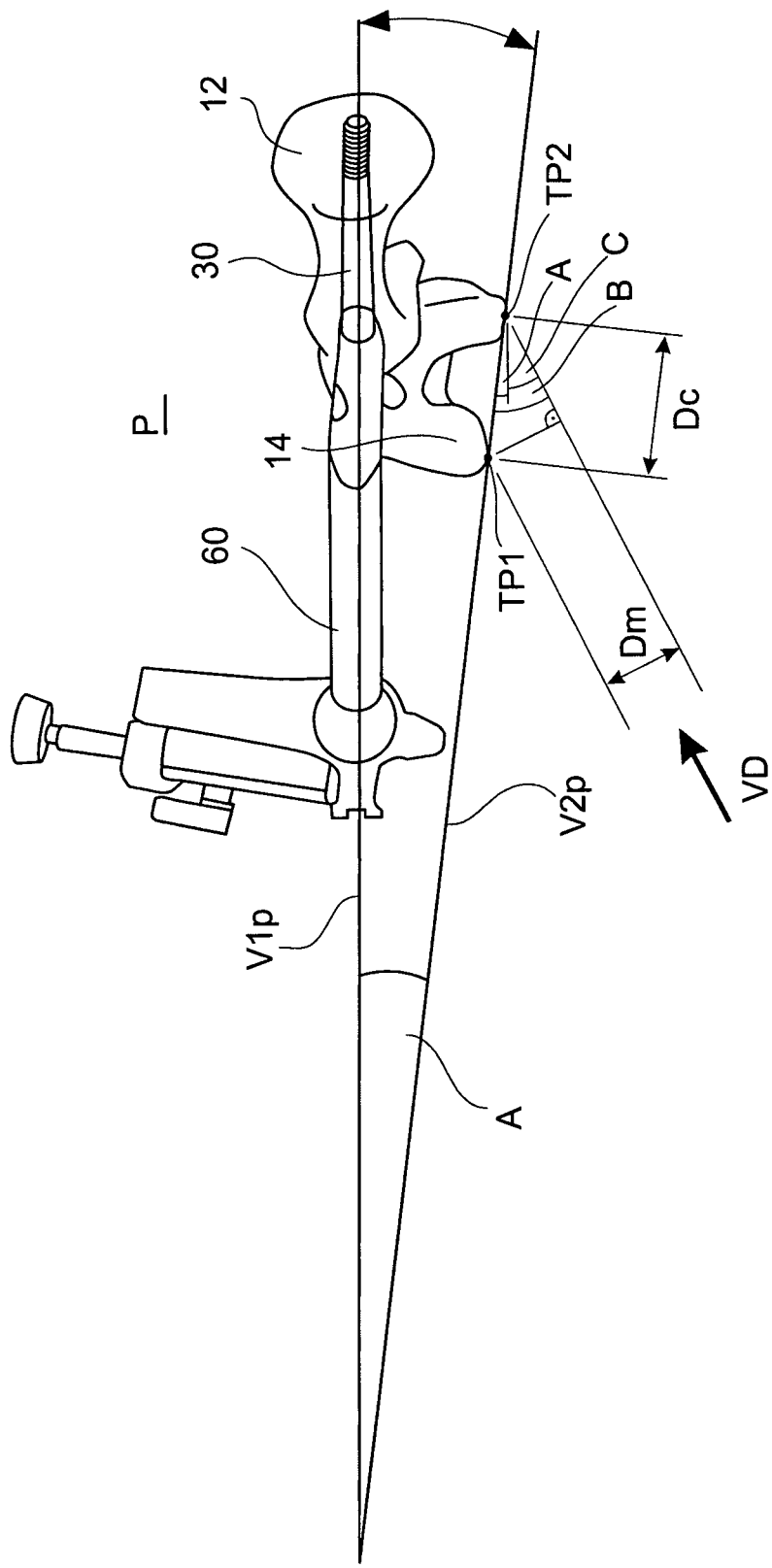
FIG. 5 illustrates an angle as a result of one embodiment of a method.

FIG. 5 is similar to FIG. 4, showing a view onto plane P. FIG. 5 differs from FIG. 4 in that an angle A is drawn in, between the first vector V1p and the second vector V2p. By means of the method such an angle A can be determined, indicating a rotational relation of a first feature at a first section and a second feature at a second section of a bone.

Figure 6:
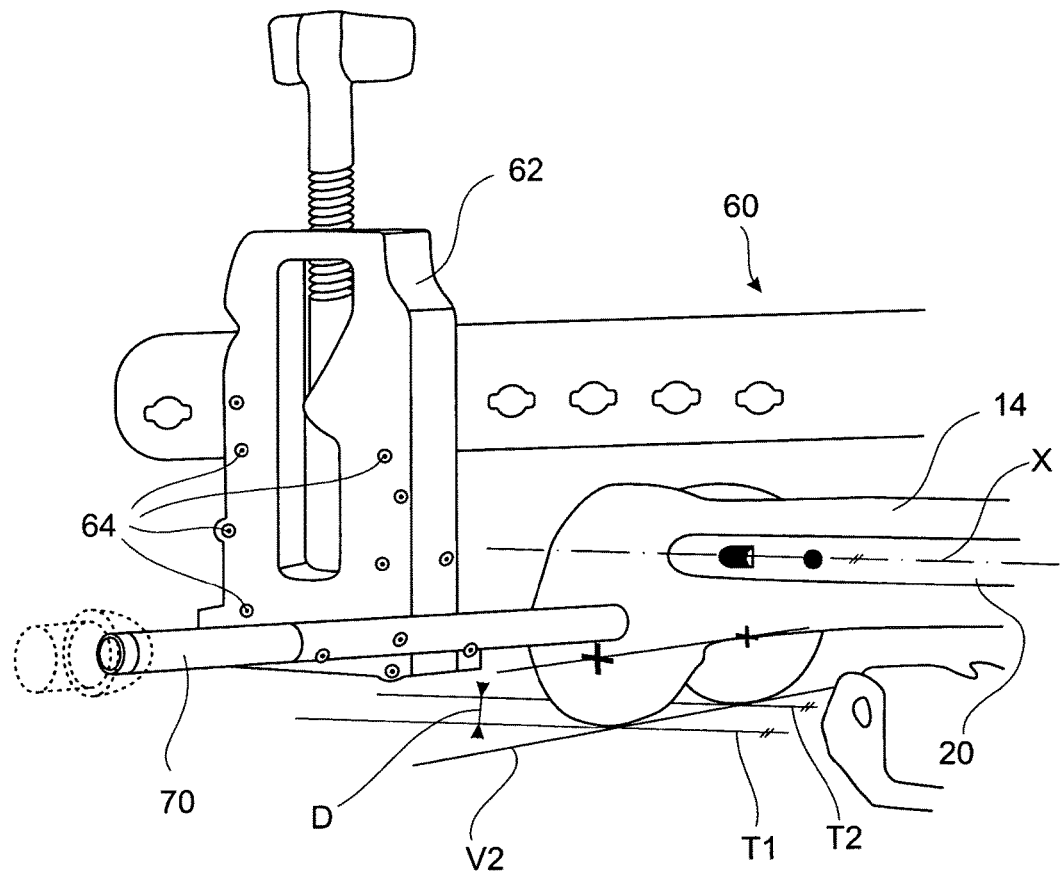
FIG. 6 shows a visualization of a distal section of a femur generated in a lateral and inclined direction.

FIG. 6 shows a schematically image which would be appropriate to determine a tangent lines at most posterior points of the condyles. The image is generated from a lateral direction but also inclined in a proximal to distal direction so that both condyles at the second section 14 of the femur can be identified in one image. Additionally shown in the image of FIG. 6, is an aiming device 60 including an adjusting element 62 for adjusting a height for inserting a locking screw through a bore in the leading end of a bone nail 20, and a sleeve 70 for facilitating the insertion of a locking screw.

Further shown in FIG. 6 is a plurality of elements 64 forming an example of a reference body. Each of these elements 64 is a small radiopaque sphere so that each element is shown as a point in an X-ray image. Due to a specific 3D distribution of the elements 64 at or within the adjusting device 62, a projection of the elements onto an imaging plane will lead to a unique 2D distribution so that an actual 3D orientation of the reference body can be determined based on the projected 2D distribution. Knowing the 3D orientation of the reference body allows the determination of an actual direction of for example a tangent line at the condyles.

By means of a single image, like that exemplarily shown in FIG. 6, it is possible to determine a second projected vector V2.

One possibility to determine the second projected vector V2 is to determine a tangent at each of the condyles, with tangent T1 defining a most posterior point at the first condyle and tangent T2 defining a most posterior point at the second condyle. Both tangents T1 and T2 may be parallel to each other as well as parallel to the longitudinal axis X of the femur. It will be understood that the height of the tangents T1, T2 differ from each other in an inclined lateral view, like that of FIG. 6. Accordingly, a distance Dm between the tangent T1 and the tangent T2 may be measured in a direction perpendicular to both tangents.

Keeping in mind that a plane is determined which is perpendicular to the longitudinal shaft axis, it will be understood that each tangent T1, T2 intersects this plane at one point. The resulting points are schematically illustrated in FIGS. 3 and 5 as points TP1 and TP2.

Further illustrated in FIG. 5 are geometrical aspects which allow a determination of an angle A between the first projected vector V1p and the second projected vector V2p. For example from a viewing direction VD, a distance Dm can be measured between the tangents T1 and T2, that is between the intersection points TP1 and TP2 of the tangents with the plane.

Based on the knowledge, for example from a data base of femurs, that dimensions at a femur have usually specific relations (with deviations), for example the width of the shaft or the diameter of the femur head relative to the distance between the condyles, the distance Dc between the condyles may be estimated from for example a measured width of the femur shaft. The angle B can therefore be calculated as arc sinus of Dm/Dc.

The angle C between the viewing direction VD and the first projected vector V1p can be determined on the basis of the orientation information which is given by the reference body. Finally, angle A can be calculated as subtraction of angle C from angle B.

While embodiments has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures can not be used to advantage.

The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

LIST OF REFERENCE SIGNS 10 bone/femur
12 first/proximal section of bone/femur
14 second/distal section of bone/femur
20 bone nail
30 locking screw
60 aiming device
62 adjusting device
64 elements of reference body
70 sleeve
100 processing means
200 imaging device
220 C-arm
240 X-ray source
260 X-ray detector
300 input device
400 monitor
500 region of interest
510 heart valve
520 actual stent
530 introduction device
540 virtual stent
600 database
A, B, C angle
Dc distance between condyles
Dm measured distance F fracture
P plane
R rotation
T1, T2 tangent
TP1, TP2 intersection point of tangent and plane
V1 first vector
V1$p$ first projected vector
V2, second vector
V2$p$, V2'$p$ second projected vector
VD viewing direction
X longitudinal axis

The invention claimed is:

1. A method for determining a rotational position of a first feature of a first bone section of a fractured bone relative to a second feature of a second bone section of the fractured bone for connecting any misalignment between the first and second bone sections caused by the bone fracture, the method comprising the steps of:

determining a longitudinal axis (X) of a bone and determining a transverse plane (P) extending perpendicular to the longitudinal axis of the bone;

determining a first projected vector (V1$p$) in the plane (P), based on a first direction defined by a feature of the first bone section of the fractured bone;

determining a second projected vector (V2$p$) in the plane (P), based on a second direction defined by a feature of the second bone section of the fractured bone;

determining an angle A between the first projected vector (V1$p$) and the second projected vector (V2$p$) to determine any anatomical misalignment between the first and second bone sections of the fractured bone;

determining from a database of non-fractured bones an angle B between the first projected vector (V1$p$) and the second projected vector (V2$p$) of a non-fracture bone; and rotating the first bone section relative to the second bone section through an angle C being the difference between angle A and angle B.

2. The method of claim 1, wherein determining at least one of the first and second projected vectors (V1$p$, V2$p$) comprises the steps of identifying at least two points at the feature of the corresponding bone section, and projecting the at least two points onto the plane (P), the two projected points (TP1, TP2) defining the projected vector (V1$p$, V2$p$).

3. The method of claim 1, wherein at least one of the longitudinal axis (X) of the bone, the feature of the first bone section and the feature of the second bone section is determined on the basis of a 3D image of at least a section of the bone.

4. The method of claim 1, wherein at least one of the longitudinal axis (X) of the bone, the feature of the first bone section and the feature of the second bone section is determined on the basis of a 2D image of at least a section of the bone, wherein the 2D image further includes a visualization of a reference body.

5. The method of claim 4, wherein the reference body comprises a structure forming a characteristic 2D projection image for determining a 3D orientation of the reference body.

6. The method of claim 4, wherein the reference body is adapted to be fixedly connected to the bone.

7. The method of claim 4, wherein the reference body is at least a part of an implant.

8. The method of claim 7, wherein the implant comprises an axis and the axis of the implant represents one of the longitudinal axis (X) of the bone, the feature of the first bone section and the feature of the second bone section.

9. The method of claim 4, wherein the reference body is adapted to be fixedly connected to the first bone section while being visible in an image showing the second bone section.

10. The method of claim 9, wherein the reference body is at least a part of an aiming device.

11. A device for determining a rotational position of a first feature of a first bone section relative to a second feature of a second bone section of a fractured bone, the device comprising a processing unit adapted for:

determining a longitudinal axis (X) of a bone based on received image data, and determining a transverse plane (P) extending perpendicular to the longitudinal axis of the bone;

determining, based on received image data, a first projected vector (V1$p$) in the plane (P), based on a first direction defined by a feature of the first bone section of a fractured bone;

determining, based on received image data, a second projected vector (V2$p$) in the plane (P), based on a second direction defined by a feature of the second bone section of a fractured bone;

determining an angle A between the first projected vector (V1$p$) and the second projected vector (V2$p$);

determining whether the angle A represents a correct alignment between the first and second sections of the fractured bone by comparing angle A to angle B of a non-fractured bone;

determining from a database of non-fractured bones an angle B between the first projected vector (VlP) and the second projected vector (V2p) of a non-fractured bone; and calculating an angle C being the difference between angles A and B for rotationally aligning the first and second bone sections.

12. The device of claim 11, further comprising an imaging unit for providing 2D projection image data of at least a section of the bone.

13. The device of claim 12, wherein the processing unit is further adapted for identifying a projection of a reference body and for determining a 3D orientation of the reference body.

14. The device of claim 11, wherein the imaging unit is adapted to provide 3D image data of at least a section of the bone.

15. A computer software which when executed on the processing unit of the device of claim 11 causes the device to perform the steps of the method of claim 1.

16. A method for determining and correcting any rotational misalignment between a proximal portion and a distal portion of a fractured femur caused by the fracture comprising:
inserting a bone nail into the fractured femur along a longitudinal axis of the fractured femur;
inserting a screw through the bone nail in an axis transverse to the longitudinal axis;
taking a digital fluoroscopic image of the bone nail, screw and fractured femur including the proximal portion and distal portion of the long bone along a viewing direction (VD);
displaying the digital image on a monitor;
defining a transverse plane perpendicular to the longitudinal axis in the displayed digital image;
projecting a first vector defined by the transverse axis of the bone screw onto the displayed transverse plane;
projecting a second vector onto the displayed transverse plane, the second vector tangent to points on the posterior medial and lateral condyles on the distal portion of the fractured femur;
using a computer to determine an angle A between the first and second vectors to determine any misalignment between the proximal and distal portions of the fractured femur by comparing the angle A between the first and second vectors of the fractured femur to an angle B between the same first and second vectors of a healthy counterpart of the fractured femur contained in a database of healthy femurs; and
rotating the proximal portion of the fractured bone about the bone nail axis with respect to the distal portion about an angle C being the difference between angle A and angle B to correct the determined misalignment.

17. The method as set forth in claim 16 wherein the healthy counterpart femur is chosen from the database of healthy femurs based on the width of the shaft or the diameter of the femoral head relative to the distance between the femoral condyles (DC) of the fractured femur.

18. The method of claim 17 further comprising measuring the distance Dm between the condyles tangent points of the second vector along the viewing direction (VD);
calculating with the computer the angle B between the viewing direction and the second vector by calculating the arc sinus of Dm/Dc, calculating the angle C between the viewing direction (VD) and the first vector;

calculating the angle between the first and second vector (angle A) by subtracting angle C from angle B;
comparing the calculated angle A to the angle between the first and second vectors on the healthy counterpart of the fractured femur to determine misalignment.

19. A method for determining a rotational position of a first feature of a proximal section of a fractured femur relative to a second feature of a distal section of the fractured femur for correcting any misalignment between the proximal and distal bone sections of the fractured bone, the method comprising:
determining a longitudinal axis (X) of a femur from an image of the femur taken along a first direction and determining a transverse plane (P) extending perpendicular to the longitudinal axis of the femur;
determining a first projected vector (V1p) in the plane (P) from the image, based on a first direction defined by an axis through a head of the proximal section of the femur;
determining a second projected vector (V2p) in the plane (P) from the image, based on a second direction defined by a line tangent to a posterior-most point on a medial and lateral condyle of the distal section of the femur;
determining an angle A between the first projected vector (V1p) and the second projected vector (V2p);
determining an angle B with a computer by estimating the distance Dc between the posterior-most target points on the condyles from a database of non-fractured femurs and a distance measured Dm between tangent posterior-most points on the condyles of the femur measured in the viewing direction on the image and calculating the arc sinus of Dm/Dc;
determining an angle C between the viewing direction of the image and vector V1p and calculating an angle A by subtracting angle C from angle B; and
rotating the proximal section with respect to the distal section through angle C to correct any misalignment.

20. The method of claim 19, wherein at least one of the longitudinal axis (X) of the bone, the feature of the first femur section and the feature of the second femur section is determined on the basis of a 2D image of at least a section of the bone, wherein the 2D image further includes a visualization of a reference body connected to the bone.

21. A method for determining a rotational position of a femoral head on a proximal section of a fractured femur relative to a medial and a lateral condyle of a distal section of the fractured femur comprising:
determining a longitudinal axis (X) of the fractured femur and determining a transverse plane (P) extending perpendicular to the longitudinal axis (X);
determining a first vector (V1p) projected onto transverse plane (P) based on a first direction defined by the direction of the femoral head of the fractured femur;
determining a second vector (V2p) projected onto transverse plane (P) based on a second direction defined by a tangent line through the posterior-most points on the medial and lateral condyles of a healthy femur selected from a database of non-fractured bones, the second vector (V2p) representing a correct alignment angle B between the first and second sections of the fractured femur;
determining an angle A between the second vector (V2p) and a third vector (V2'p) based on a third direction defined by a tangent line through the posterior-most points on the medial and lateral condyles of the fractured femur, angle A representing the incorrect rotational alignment of the first and second sections of the fractured femur; and determining an angle C being the difference between angle A and B representing the angle which the proximal and distal sections must be rotated to correct misalignment.

22. The method of claim 21 wherein the second vector (V2$p$) is determined from an image of a healthy counterpart femur of a patient.

23. The method of claim 22 wherein the first vector (V1$p$) and the third vector (V2'p) are determined from a three-dimensional image of the fractured femur.

* * * * *